(12) United States Patent
Barrett

(10) Patent No.: US 9,336,195 B2
(45) Date of Patent: May 10, 2016

(54) METHOD AND SYSTEM FOR DICTIONARY NOISE REMOVAL

(71) Applicant: Nuance Communications, Inc., Burlington, MA (US)

(72) Inventor: Neil D. Barrett, Montreal (CA)

(73) Assignee: Nuance Communications, Inc., Burlington, MA (US)

( * ) Notice: Subject to any disclaimer, the term of this patent is extended or adjusted under 35 U.S.C. 154(b) by 230 days.

(21) Appl. No.: 14/010,903

(22) Filed: Aug. 27, 2013

(65) Prior Publication Data

US 2015/0066485 A1     Mar. 5, 2015

(51) Int. Cl.
*G06F 17/27*     (2006.01)
*G06F 17/30*     (2006.01)
*G06F 19/00*     (2011.01)

(52) U.S. Cl.
CPC ...... *G06F 17/2735* (2013.01); *G06F 17/30737* (2013.01); *G06F 19/345* (2013.01)

(58) Field of Classification Search
CPC ..... G06F 17/27; G06F 17/20; G06F 17/2705; G06F 17/271; G06F 17/2715; G06F 17/272; G06F 17/2725; G06F 17/273; G06F 17/2735; G06F 17/274; G06F 17/2745; G06F 17/275; G06F 17/2755; G06F 17/276; G06F 17/2765; G06F 17/277; G06F 17/2775
See application file for complete search history.

(56) References Cited

U.S. PATENT DOCUMENTS

| | | | | |
|---|---|---|---|---|
| 4,862,408 A | * | 8/1989 | Zamora | |
| 4,887,212 A | * | 12/1989 | Zamora et al. | 704/8 |
| 5,251,290 A | * | 10/1993 | Pabon | 345/420 |
| 6,253,169 B1 | * | 6/2001 | Apte et al. | 704/9 |
| 7,644,085 B2 | * | 1/2010 | Miller et al. | 707/797 |
| 8,762,130 B1 | * | 6/2014 | Diaconescu et al. | 704/9 |
| 8,762,131 B1 | * | 6/2014 | Diaconescu et al. | 704/9 |
| 8,954,399 B1 | * | 2/2015 | Balakrishnan et al. | 707/692 |
| 9,058,393 B1 | * | 6/2015 | Nicks et al. | |
| 2003/0171926 A1 | * | 9/2003 | Suresh et al. | 704/270.1 |
| 2004/0243396 A1 | * | 12/2004 | Liu et al. | 704/10 |
| 2007/0265829 A1 | * | 11/2007 | Turner et al. | 704/9 |
| 2007/0282607 A1 | * | 12/2007 | Bond et al. | 704/260 |

(Continued)

OTHER PUBLICATIONS

Lee et al., Web scale taxonomy cleansing, 2011, Proceedings of the VLDB Endowment, vol. 4 No. 12, pp. 1295-1306.*
Nakashole et al., PATTY: a taxonomy of relational patterns with semantic types, 2012, Proceedings of the 2012 Joint Conference on Empirical Methods in Natural Language Processing and Computational Natural Language Learning, Association for Computational Linguistics, pp. 1135-1145.*

(Continued)

*Primary Examiner* — Lamont Spooner
(74) *Attorney, Agent, or Firm* — Wolf, Greenfield & Sacks, P.C.

(57) ABSTRACT

A method and system of removing noise from a dictionary using a weighted graph is presented. The method can include mapping, by a noise reducing agent executing on a processor, a plurality of dictionaries to a plurality of vertices of a graphical representation, wherein the plurality of vertices is connected by weighted edges representing noise. The plurality of dictionaries may further comprise a plurality of entries, wherein each entry further comprises a plurality of tokens. The method can include selecting a subset of the weighted edges, constructing an acyclic graphical representation from the selected subset of weighted edges, and determining an ordering based on the acyclic graphical representation. The selected subset of weighted edges may approximate a solution to the Maximum Acyclic Subgraph problem. The method can include removing noise from the plurality of dictionaries according to the determined ordering.

20 Claims, 7 Drawing Sheets

(56) References Cited

U.S. PATENT DOCUMENTS

| | | | | |
|---|---|---|---|---|
| 2008/0312910 | A1* | 12/2008 | Zhang | 704/10 |
| 2009/0254817 | A1* | 10/2009 | Dreyfus et al. | 715/257 |
| 2010/0153880 | A1* | 6/2010 | Dinn | 715/816 |
| 2010/0153881 | A1* | 6/2010 | Dinn | 715/825 |
| 2011/0004488 | A1* | 1/2011 | Benja-Athon | 705/2 |
| 2011/0125813 | A1* | 5/2011 | Pradhan et al. | 707/814 |
| 2011/0208513 | A1* | 8/2011 | Nicks et al. | 704/10 |
| 2011/0208723 | A1* | 8/2011 | Nicks et al. | 707/723 |
| 2014/0074764 | A1* | 3/2014 | Duftler et al. | 706/47 |

OTHER PUBLICATIONS

Lee et al., Web scale entity resolution using relational evidence, 2011, Technical report, Microsoft Research, 2011. Available at http://research.microsoft.com/apps/pubs/default.aspx, pp. 1-11.*

Brauer et al., Graph-based concept identification and disambiguation for enterprise search, 2010, Proceedings of the 19th international conference on World wide web, ACM, pp. 171-180.*

* cited by examiner

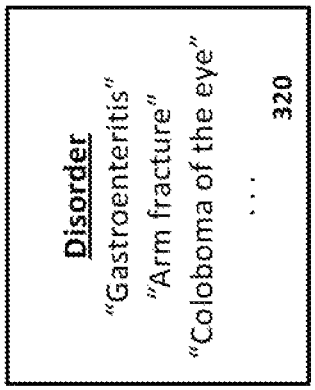
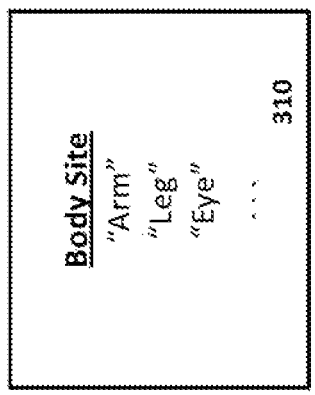
FIG. 3A
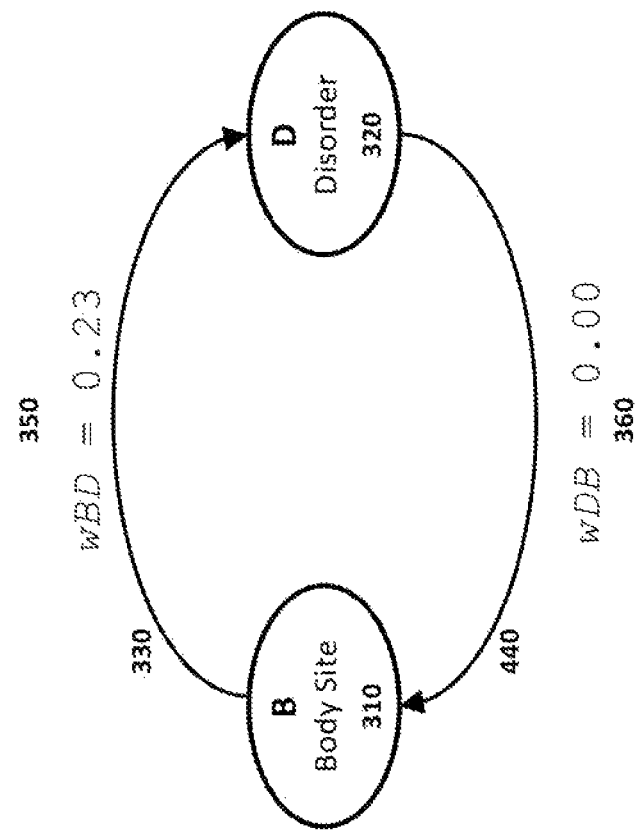
FIG. 3B

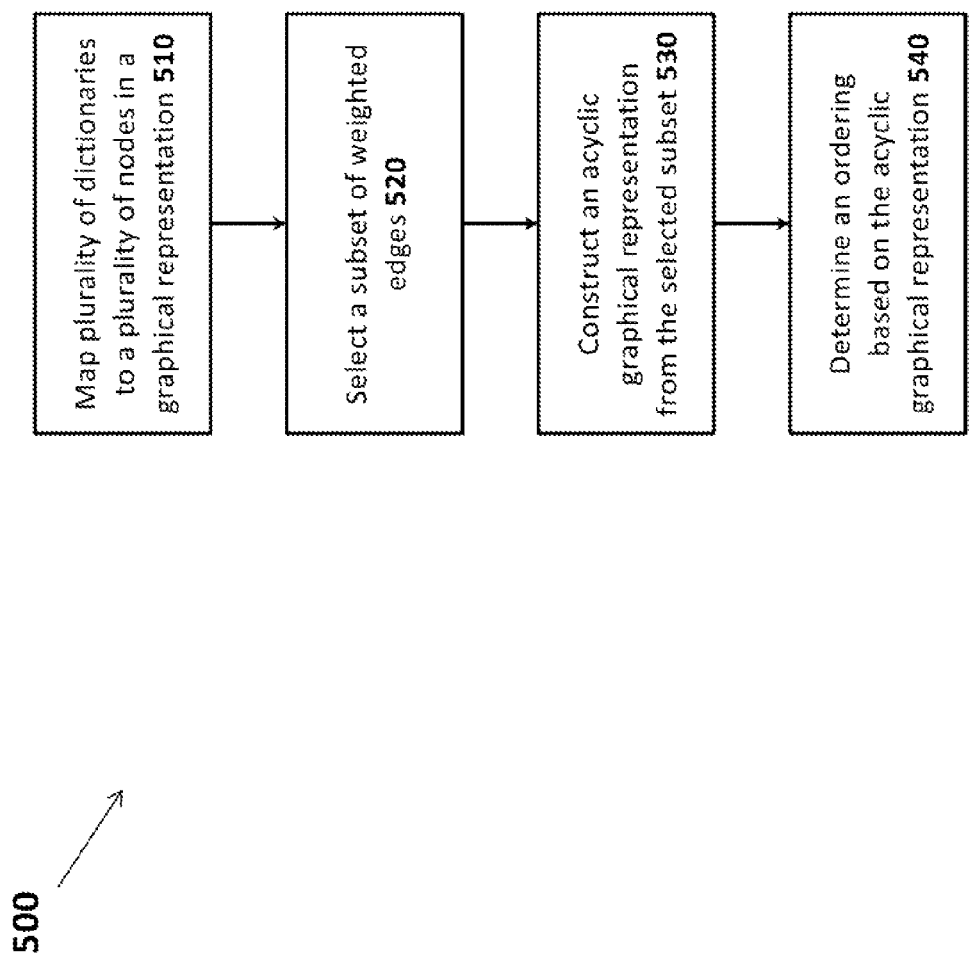

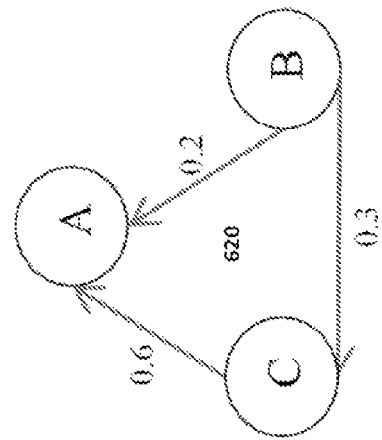
A graph  FIG. 6A
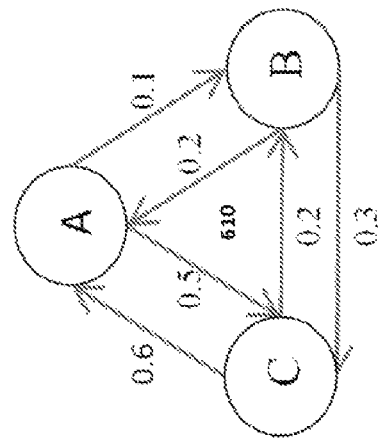
Incorrect (cycle)  FIG. 6C
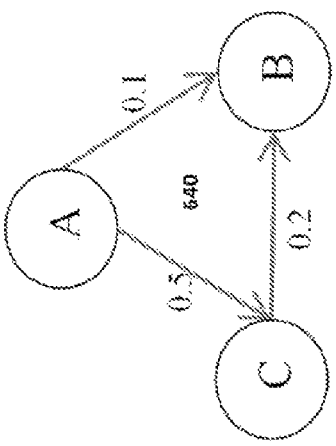
Solution  FIG. 6B
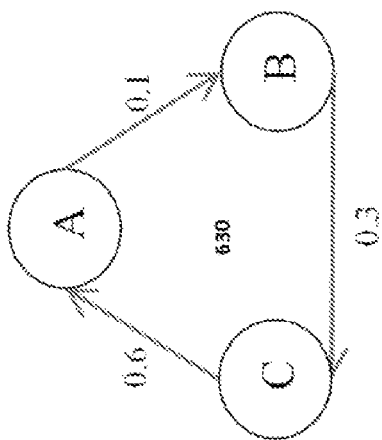
Incorrect (weight)  FIG. 6D

METHOD AND SYSTEM FOR DICTIONARY NOISE REMOVAL

FIELD OF THE DISCLOSURE

The present disclosure relates to a method for removing noise from dictionaries.

BACKGROUND

Machine learning algorithms, such as artificial neural networks, decision trees, and support vector machines, are able to recognize patterns in a new data set after first being trained on a learning data set. Such algorithms have been used to filter spam emails, perform optical character recognition, counter credit card fraud, and understand the intent of a speaker from a spoken sentence. Generally, as the learning data set increases in size and the algorithm gains experience, its ability to correctly recognize patterns within new data improves. However, supplying a comprehensive learning data set may not be possible due to size and time constraints. In these cases, dictionaries can be used to augment the ability of a machine learning algorithm to apply previously learned patterns to new data.

Dictionaries can improve the performance of machine learning algorithms in a variety of ways. For example, a dictionary could simply contain data entries that were not initially present during the training phase, thus increasing the size of the effective learning data set. Dictionaries can also expand a machine learning algorithm's ability to recognize data as belonging to a class or category, aiding in pattern recognition. For example, a part-of-speech tagging algorithm can be trained to mark words in text as corresponding to parts of speech, such as nouns and verbs. Providing the algorithm with dictionaries of words classified as nouns or verbs allows it to recognize patterns learned from a limited initial data set to a much broader one.

Given their utility, dictionaries with many entries are preferred. Typically, entries are collected automatically through the use of automated scripts and programs, because manual compilation is time consuming. For example, in the fields of natural language processing and understanding, efforts have focused on extracting dictionaries directly from raw source data. One technique includes extending previous categorizations in manually annotated data to non-annotated data. Another technique includes extending manually constructed rules or templates over source data, such as pattern matching with regular expressions. The results are dictionaries containing entries captured by either the categorization or template. Researchers have also explored transforming preexisting databases into dictionaries using defined rules and heuristics.

One problem with automatically created dictionaries is the high level of entry duplication found in the created dictionaries. Entry duplication between dictionaries creates "noise." This noise causes the algorithm to be unable to distinguish an entry as unique to a single dictionary. On a larger scale, duplication between dictionaries and the subsequent associated noise may hinder the utility of dictionaries for machine learning purposes. Previously, work has focused on improving the process of automatic dictionary creation to produce dictionaries with less noise. What is needed is an improved method for reducing noise in dictionaries.

SUMMARY

Creating dictionaries manually is a time consuming process. However, the automatic creation of dictionaries generally suffers from entry duplication and noise. The present disclosure solves these problems by removing noise from dictionaries of any source. Further, the present disclosure uses a novel method that maps dictionary noise to a weighted graph and determines an optimal ordering for noise removal.

In one embodiment, a method, and corresponding system, of removing noise from a dictionary using a weighted graph includes mapping, by a noise reducing agent executing on a processor, a plurality of dictionaries to a plurality of vertices of a graphical representation. The plurality of vertices is connected by weighted edges that represent noise. A subset of the weighted edges is selected and used to construct an acyclic graphical representation. An ordering is determined based on the acyclic graphical representation, and noise is then removed from the plurality of dictionaries according to the determined ordering.

In another embodiment, the method and system can include mapping a plurality of dictionaries to a plurality of vertices such that each dictionary is represented by one vertex.

In yet a further embodiment, each vertex is connected to another vertex by an incoming weighted edge representing noise that can be removed from the vertex's mapped dictionary, and an outgoing weighted edge representing noise that can be removed from the connected vertex's mapped dictionary.

In an additional embodiment, the ordering is determined based on the acyclic graphical representation by starting from vertices having no outgoing weighted edges and progressing to vertices having only outgoing weighted edges.

In an additional embodiment, the method and system can include mapping a plurality of dictionaries comprising a plurality of entries, wherein each entry further comprises a plurality of symbols.

In an additional embodiment, removing noise from the plurality of dictionaries further comprises removing entries.

In an additional embodiment, removing noise from the plurality of dictionaries further comprises removing tokens.

In an additional embodiment, the method and system can include selecting a subset of the weighted edges that approximates a solution to the Maximum Acyclic Subgraph problem.

In an additional embodiment, the method and system can include creating the plurality of dictionaries from an ontology.

In an additional embodiment, the method and system can include providing the dictionaries to a language processing system.

BRIEF DESCRIPTION OF THE DRAWINGS

FIGS. 1 through 7, wherein like parts are designated by like reference numerals throughout, illustrate an example embodiment of a system and method for the implementation of a noise reducing agent for reducing noise in dictionaries. Although the present disclosure describes said method with reference to the example embodiments illustrated in the figures, it should be understood that many alternative forms can embody the present disclosure. One of ordinary skill in the art will additionally appreciate different ways to alter the parameters of the embodiments disclosed in a manner still in keeping with the spirit and scope of the present disclosure.

FIG. 1 is a block diagram illustrating an embodiment of a system for removing noise from dictionaries.

FIG. 2 is a block diagram illustrating another embodiment of a system for removing noise from dictionaries.

FIGS. 3A-3B are block diagrams illustrating the concept of dictionary noise in an embodiment of the present disclosure.

FIG. 4 is a flow diagram illustrating an embodiment of a method of removing noise from dictionaries.

FIG. 5 is a flow diagram illustrating a method of determining the ordering of noise removal from a plurality of dictionaries.

FIGS. 6A-6D are graphs that illustrate the Maximum Acyclic Subgraph (MAS) problem and its application to noise removal.

FIG. 7 is a flow diagram illustrating a method of removing noise from dictionaries according to a determined ordering.

DETAILED DESCRIPTION OF THE DISCLOSURE

The present disclosure features a novel approach to reducing noise in dictionaries. As discussed above, past efforts to create dictionaries with a low level of noise focused on the step of dictionary creation. The present system and method permit a separation between the process of dictionary creation and the process of noise removal. The present system and method can be used within the automatic creation of dictionaries, or applied to dictionaries that have already been created. Further, the present system and method can be performed repeatedly on an entire set or subset of dictionaries.

As utilized herein, the term "dictionary" may refer to any set of words or phrases. Each dictionary may comprise a plurality of entries, which in turn may comprise a plurality of words, characters, symbols, or tokens. A dictionary may include only entries within a single category or class, wherein the entries within a single category or class have a common shared property, such as a set of colors, prime numbers, or groceries. A dictionary may be given a name reflecting its represented class. Dictionaries can be used for a variety of purposes. For example, dictionaries can be used to improve the performance of machine learning algorithms.

Figure 1:
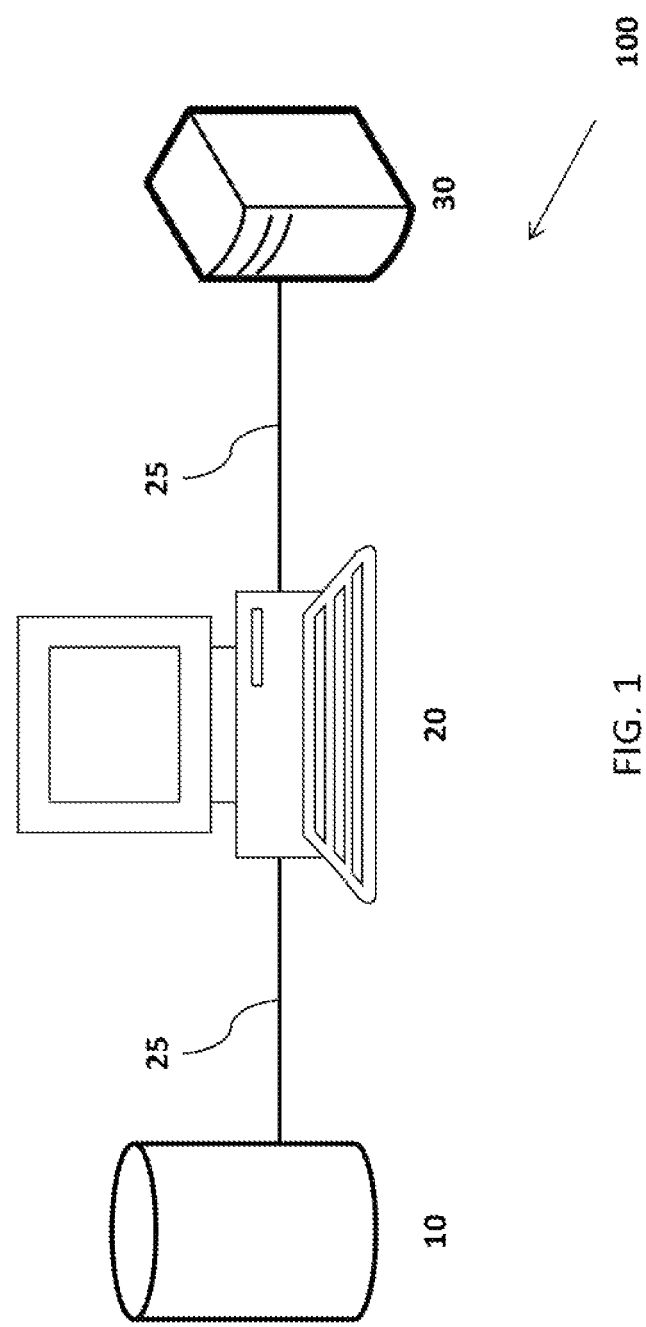

FIG. 1 is a block diagram illustrating an example embodiment of a noise reducing system 100. The noise reducing system 100 comprises a dictionary content source 10 connected to a computing device 20 by a communications link 25. The noise reducing system 100 further comprises a machine learning system 30, which is connected to the computing device 20 by a communications link 25.

The noise reducing system 100 may generate dictionaries automatically from the dictionary content source 10. The dictionary content source 10 can be any data source or service that contains entries suitable for storing within a dictionary. In this embodiment and as explained above, entries may comprise words, characters, symbols, or any combination thereof. Further, the dictionary content source 10 may contain additional relationship information that can be used to help identify entries belonging to a class or category. The dictionary content source 10 may also be a pre-generated set of dictionaries. When dictionaries are pre-generated, the noise reducing system 100 can simply retrieve dictionaries from the dictionary content source 10.

In one embodiment, the dictionary content source 10 is a medical ontology. An ontology represents information as a set of concepts, including relationships between pairs of concepts. Ontologies are useful for creating dictionaries because the embedded relationships may be explored to help identify entries belonging to a class or category. A medical ontology may be used to build dictionaries representing illnesses, treatments, body sites, or other categories. A suitable medical ontology for this purpose could be SNOMED CT, a medical ontology containing a comprehensive list of clinical and healthcare terms. The resulting dictionaries could then be provided to a to a machine learning algorithm that can recognize those classes of information. It should be noted that the present disclosure is not limited to medical ontologies, but rather can use or create dictionaries from any source.

In one embodiment, the machine learning system 30 is a machine learning algorithm implemented as a part of a clinical language understanding (CLU) system. The CLU system, when presented with new, previously unseen words, can reference dictionary entries in order to determine a class or category for the newly seen words. Dictionaries with many entries, such as those generated from an ontology representing a comprehensive healthcare terminology, will increase the likelihood of a given word being recognized as belonging to a class. Thus, the CLU system can use dictionaries created from a medical ontology to better apply patterns learned from previously seen illnesses, treatments, and other healthcare-related classes to new, previously unseen data.

The computing device 20 may be a workstation, server, desktop computer, laptop, handheld computer, cell phone, mobile device, or any other computer system. In some embodiments, the computing device may be wearable, for example, by being connected to a wrist watch, pair of glasses, or article of clothing. The computing device 20 may have sufficient processing power and memory to perform all or part of the operations described herein, or alternately may only serve as a proxy for operations performed off-site.

The computing device 20 may access the dictionary content source 10 via the communications link 25. The communications link 25 may comprise any communication means, including TCP/IP over a LAN or WAN network, or a direct connection such as USB or SATA. Similarly, the machine learning system 30 may access the dictionaries via the communications link 25 by a variety of means, or even simply by transferring the dictionaries manually with a thumb drive or disk. Further variations will be evident to those skilled in the art.

In one embodiment, the computing device 20 may contain a script that directly queries the dictionary content source 10 in order to access or build dictionaries. If it needs to build dictionaries, the computing device 20 automatically generates a set of dictionaries corresponding to a set of classes or categories. The categories may be pre-determined, or automatically generated according to information present within the dictionary content source 10. As discussed above, automatically created dictionaries may contain a high level of noise. The computing device 20 may then process the dictionaries to reduce noise, thus creating a set of "cleaned" dictionaries. The cleaned dictionaries may then be used for a variety of purposes, including for use by a machine learning system 30.

It should be noted that the present system and method can remove noise from dictionaries from any source, not just those generated from a medical ontology. Similarly, the cleaned dictionaries generated by the disclosed embodiments can be used for any purpose, not just for use by a CLU system or other machine learning system.

Figure 2:
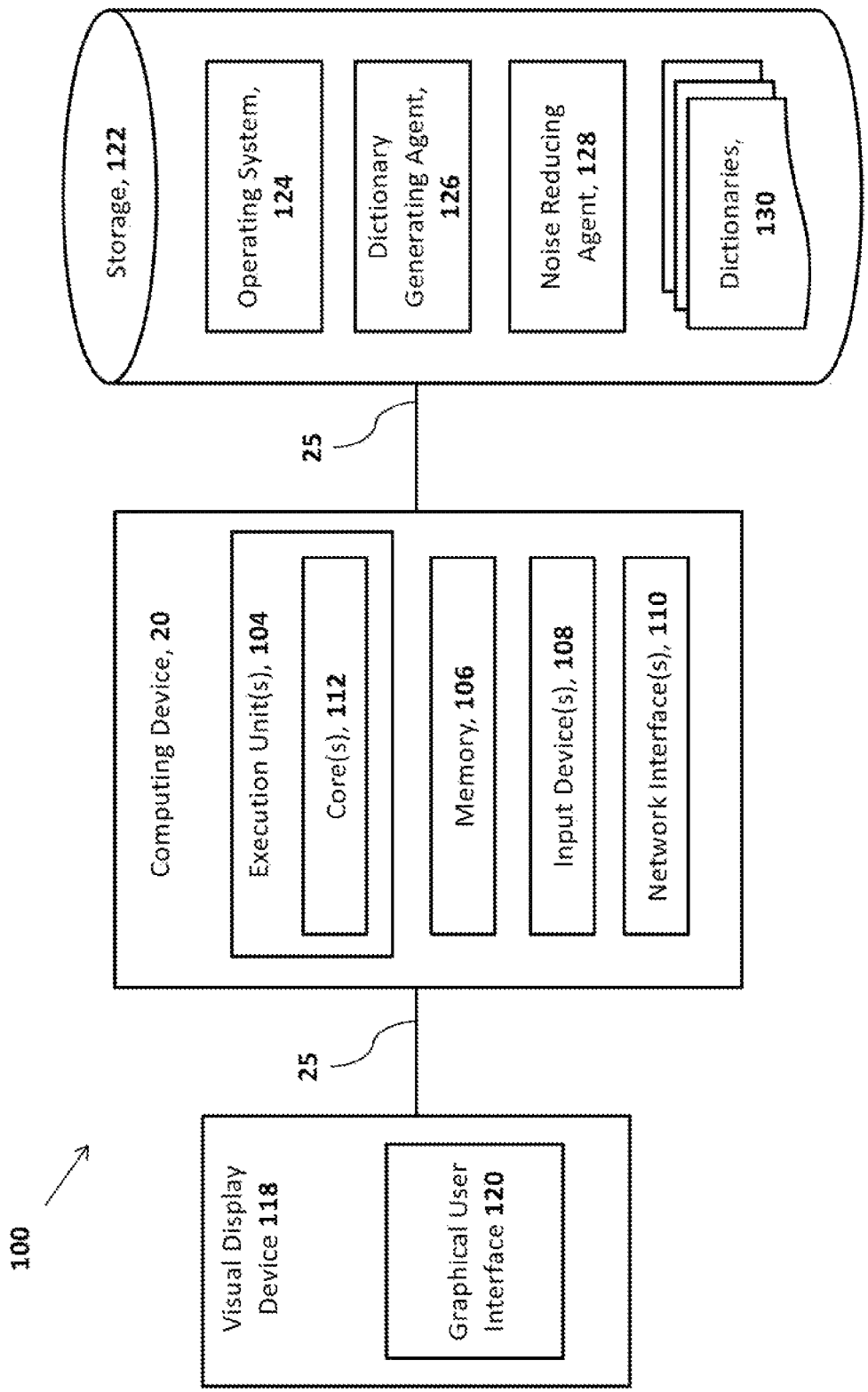

FIG. 2 depicts another embodiment of the noise reducing system 100 suitable for practicing exemplary embodiments of the present disclosure. The noise reducing system 100 includes a computing device 20, which may include execution unit(s) 104, memory 106, input device(s) 108, and network interface(s) 110. A user may interact with the computing device 20 through a visual display device 118, such as a computer monitor or mobile display, which may include a graphical user interface (GUI) 120. The visual display device may be connected to the computing device by a communications link 25. The noise reducing system 100 may further comprise a storage device 122, such as a hard-drive, flashdrive, DVD, or CD-ROM, for storing an operating system 124 and other software programs, such as a dictionary generating agent 126 and a noise reducing agent 128. The storage device 122 may also be connected to the computing device 20 by a communications link 25. Further, the storage device 122 may store a plurality of dictionaries 130.

The execution unit(s) 104 may include hardware or software based logic to execute instructions on behalf of the computing device 20. For example, depending on specific implementation requirements, execution units 104 may include: one or more processors, such as a microprocessor; single or multiple cores 112 for executing software stored in the memory 106, or other programs for controlling the computing device 20.

The computing device 10 may include other I/O devices, such as a keyboard and a pointing device (for example, a mouse) for receiving input from a user. Optionally, the keyboard and the pointing device may be connected to the visual display device 118, which may also feature touch- or gesture-based interaction. The computing device 20 may include other suitable conventional I/O peripherals.

Depending on particular implementation requirements of the present disclosure, the computing device 20 may be any computing system such as a workstation, desktop computer, server, laptop, handheld computer, cell phone, mobile device, or other appropriate form of computing device. The computing device 20 may have sufficient processing power and memory capacity to perform all or part of the operations described herein, or alternately may only serve as a proxy, with many of its functions, performed externally by a server or other computing device. In some embodiments, the computing device may be wearable and connected to a wrist watch, pair of glasses, or article of clothing.

The storage device 122 may be any form of storage, such as a hard disk, solid state drive, or cloud-based storage. The storage device 122 may connect to the computing device 20 by the communications link 25, which may comprise a direct or networked connection, including but not limited to any of the means described above for suitable communications links. The dictionary generating agent 126 and noise reducing agent 128 may run on any operating system 124, including any of the versions of the conventional operating systems, any embedded operating system, any real-time operating system, any open source operating system, any proprietary operating system, any operating systems for mobile computing devices, any thin-client operating system, or any other operating system capable of running on the computing device and performing part or all of the operations described herein. Furthermore, the operating system 124, dictionary generating agent 126, and noise reducing agent 128 may in some instances be run from a bootable CD, thumb drive, or from a network.

The storage device 122 may also comprise a plurality of dictionaries 130. The plurality of dictionaries may be generated by the dictionary generating agent 126, or alternately could be pre-generated or manually compiled. The plurality of dictionaries may come from any source and may be stored in any manner or format, such as within a database or flat-file.

As discussed above, a goal in dictionary creation is to compile as many entries as possible. In one embodiment, the dictionary generating agent 126 creates dictionaries automatically by querying the dictionary content source 20, in this case a medical ontology, for entries relating to a set of medical categories. For example, the categories could include "disorder" or "body site." The dictionary generating agent 126 explores relationships and concepts within the medical ontology to identify entries relevant to each medical category, and then places them into an appropriate set of dictionaries, creating the plurality of dictionaries 130. For example, a resulting "illness" dictionary generated from an ontology might contain entries such as "pneumonia," "strep throat," and "malaria," and a resulting "body site" dictionary might contain a list of body structures such as "arm," "leg," and "torso." The plurality of dictionaries 130 may then be provided to a CLU system to improve performance, or first be cleaned by the noise reducing agent 128.

FIGS. 3A-3B illustrate one concept of dictionary noise in an embodiment of the present system in more detail. As discussed above, in one embodiment, a common drawback to automatically created dictionaries is a high level of noise due to duplicated words. In order for a dictionary entry to be useful, it is helpful for a machine learning algorithm to identify it as unique to a single dictionary. For example, as illustrated in FIG. 3A, consider a "body site" dictionary 310 that includes the entry "arm," and a "disorder" dictionary 320 that includes the entry "arm fracture." The word "arm" is duplicated, as it is indicated as belonging to both the "body site" and "disorder" classes. A machine learning algorithm would not be able to reference the "body site" and "disorder" dictionaries to determine whether a physician dictating the words "arm fracture" is referring to a body site or disorder (though it may still be able to make that determination based on a specific context). Thus, there is noise between the "body site" and "disorder" dictionaries, resulting in a machine learning algorithm that has no improvement in pattern recognition for the term "arm fracture."

If the word "arm" is removed from one of the dictionaries, however, then the associated noise from duplication has been eliminated. Initially, it is difficult to choose the "best" dictionary from which to remove a duplicated word, because removing a word from a dictionary may result in a decreased utility of that dictionary for providing new words related to a class or category. Additionally, as the number of dictionaries increases, the order of removing words from dictionaries becomes important as words may be duplicated in multiple dictionaries. Ideally, noise removal should be performed in a manner that removes a maximum amount of noise from the plurality of dictionaries, while maintaining the utility of the dictionaries for improving machine learning tasks such as language understanding tasks and pattern recognition.

In order to determine the manner and quantity of noise removal, the level of noise between dictionaries may first be calculated and then visualized by a dependency graph. In one embodiment of the present disclosure, the noise reducing agent 128 calculates a measure of noise between two dictionaries. A dependency graph is then created with nodes/vertices connected by edges. The dictionaries are mapped to the nodes, and the calculated noise values are mapped to the edges as weights, creating weighted edges. FIG. 3B illustrates how the dictionaries and calculated noise values can be visualized in such a manner. In this example, an edge (B,D) 330 represents entries in "body site" that are present in "disorder." Similarly, an edge (D,B) 340 represents entries in "disorder" that are present in "body site." The noise reducing agent 128 assigns noise levels as weights 350 360 to the directed edges 330 340. Once the graph is complete, the noise reducing agent then considers the weights and directed edges in order to determine an optimal process for noise removal, as described in more detail below.

Figure 4:
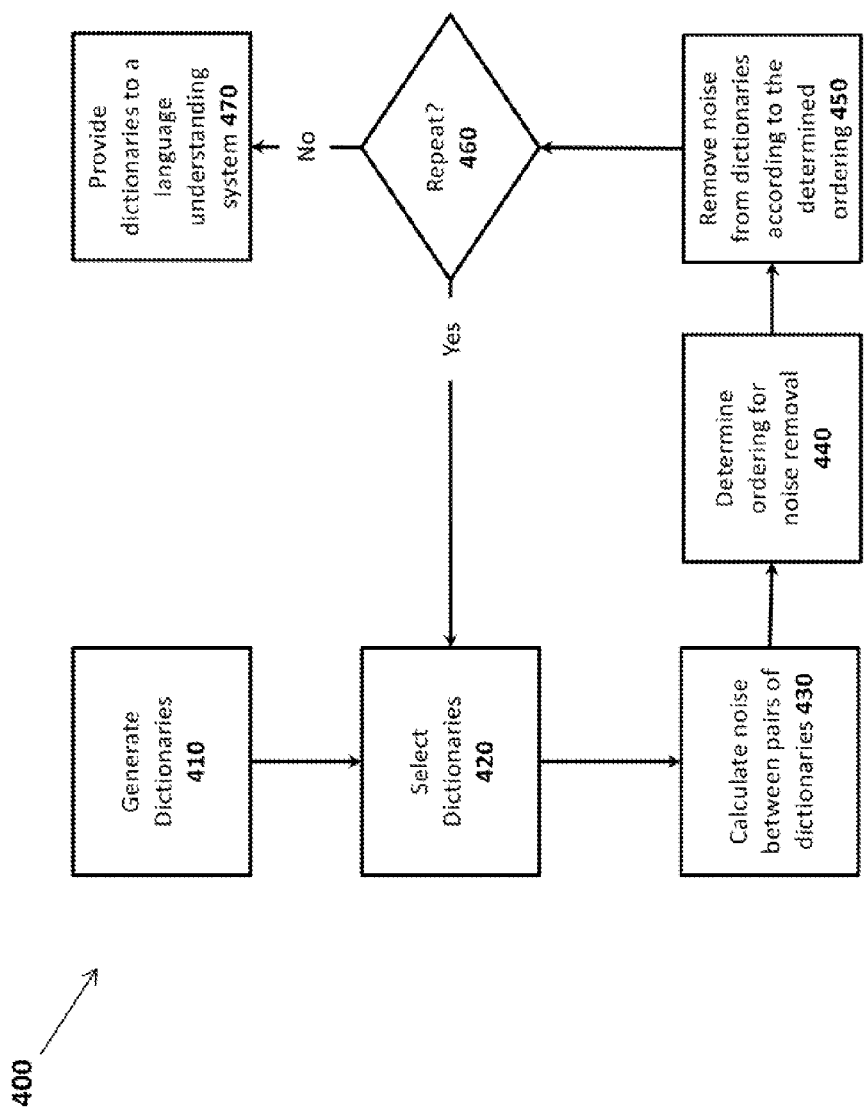

FIG. 4 is a flow diagram illustrating a method of removing noise from dictionaries in accordance with an embodiment of the instant disclosure. The method 400 can be performed in the context of a noise reducing system 100, or by any other system or method that utilizes dictionaries. Removing noise from dictionaries may include a noise reducing agent automatically creating a plurality of dictionaries from a dictionary content source (step 410). The noise reducing agent then selects a set or subset of the plurality of dictionaries for noise removal and cleaning (step 420). The selection of dictionaries for cleaning may be chosen by a person choosing particular dictionaries for cleaning, or alternately by a script that does so automatically. The noise reducing agent then calculates the level of noise between every pair of the selected dictionaries (step 430), uses the calculated levels to determine an ordering for noise removal (step 440), and removes noise from the dictionaries according to the determined ordering (step 450). If necessary, the method 400 can be repeated (step 460) in order to accommodate the addition or removal of other dictionaries to the process. Once noise removal is complete, the dictionaries may be provided to a clinical language understanding system, or alternately, used for any purpose (step 470).

Once the dictionaries are selected (step 420), noise calculation identifies those dictionaries with high levels of noise, thus indicating which dictionaries possess the most noise to remove (step 430). As discussed above, in one embodiment, noise is a result of duplication of terms between pairs of dictionaries. Some dictionaries may have more duplicated words, and thus more noise, than others. A dictionary with a relatively high level of noise would be a dictionary that has many duplicated entries as compared to other dictionaries. Noise may also represent other types of overlap or duplication between dictionaries.

Noise removal can be accomplished in a variety of ways. In one embodiment, noise is removed by deleting entries in one dictionary that are present in another. However, in alternate embodiments, the noise reducing agent could remove only portions of an entry, individual words, symbols, or tokens in order to reduce noise.

Noise removal may proceed by determining an ordering (step 440). In this embodiment, noise removal is ordered, because removing entries from a single dictionary will affect what entries would be removed from other dictionaries. This may begin by mapping the dictionaries and calculated noise levels to a weighted graph, wherein the dictionaries are represented by nodes/vertices and the noise levels are represented by weighted edges. Once the weighted graph is complete, a subset of the weighted edges is selected such that the graph becomes acyclic, creating an acyclic subgraph. The ordering specified by the acyclic subgraph is then used to order the removal of noise from the dictionaries.

In one embodiment, the noise reducing agent follows an ordering determined from the acyclic subgraph, traversing the subgraph and performing deletions within the dictionary represented by each node it selects (step 450). The noise reducing agent performs deletions starting from nodes having no outgoing edges, and progressing to nodes having only outgoing edges. Once the noise reducing agent selects a node as a starting point, the noise reducing agent follows the path of the acyclic graph, removing noise from dictionaries and thus "treating" each node. The noise reducing agent repeats this process until all nodes have been treated. The procedure for ordering noise removal in one embodiment of the present disclosure is described in more detail below.

If necessary, the method 400 can be repeated (step 460) in order to accommodate the addition, or removal of other dictionaries to the process. In some embodiments, it may be advantageous to further "clean up" the results of noise removal. A first round of noise removal may yield many valueless entries containing "on," "of," and "in," because the words previously associated with these entries have been removed. These entries could then be removed in a second round of cleaning that incorporates specialized dictionaries with entries that are limited to linking or transition words. Here, it may be preferable to limit noise removal to only entries that perfectly match in order to maintain relationships between words. For example, a clinician presented with a "parasite in leg" may have a different prognosis than one presented with a "parasite on leg."

It should be noted that the process for noise removal can apply to dictionaries and entries of any type. The dictionaries may contain single words, symbols, tokens, or combinations thereof. Further, the embodiments of the present disclosure may use any process or measure for calculating the level of noise within dictionaries.

FIG. 5 is a flow diagram illustrating a method 500 of determining the order of noise removal from a plurality of dictionaries. In this embodiment, the problem of ordering noise removal from dictionaries is mapped to the maximum acyclic subgraph (MAS) problem. The method 500 may begin with a noise reducing agent mapping a plurality of dictionaries to a plurality of nodes/vertices in a graphical representation, such as a weighted graph (step 510) (as shown and described in FIGS. 4B, 6). Calculated noise levels for each pair of dictionaries are assigned as weights to the directed edges connecting each node to every other node. The noise reducing agent selects a subset of the directed edges (step 520) to create an acyclic graphical representation, or weighted graph (step 530). The noise reducing agent 128 then determines an ordering for removing noise from dictionaries from the acyclic weighted graph (step 540). The ordering is determined based on a solution to the MAS problem.

Though steps 520 and 530 are separated in method 500, they may occur at the same time. For example, one may simply construct an acyclic graphical representation by selecting a subset of weighted edges.

FIGS. 6A-6D are graphs that provide a further illustration of the MAS problem and its application to noise removal. Graph 610 has three nodes representing dictionaries A, B, and C. A noise reducing agent maps calculated noise levels for each pair of dictionaries to the edges as weights, wherein the noise levels correspond to noise that can be removed. The ideal solution 620 will result in an acyclic graph that maximizes the sum of the weights (i.e., the sum of edges BA, CA, and BC which equals 1.1). The resulting acyclic dependency graph provides a partial ordering over the dictionaries, specifying the order in which dictionary noise should be removed. Other solutions include those where the resulting graph is not acyclic 630, and those where the graph is acyclic, but the sum of weights is not optimal 640 (0.8).

The MAS problem is within a class of problems in computational complexity theory that are known as "NP-hard." Consequently, an optimal solution to the MAS problem may be time consuming to compute. Fortunately, many algorithms exist to approximate a solution to the MAS problem. For example, a simple algorithm could order the directed edges by weight and iteratively include edges in the solution, starting with the highest weighted edge, as long as a cycle is not created. Other algorithms and approximations will be known to those skilled in the art and are incorporated herein.

Figure 7:
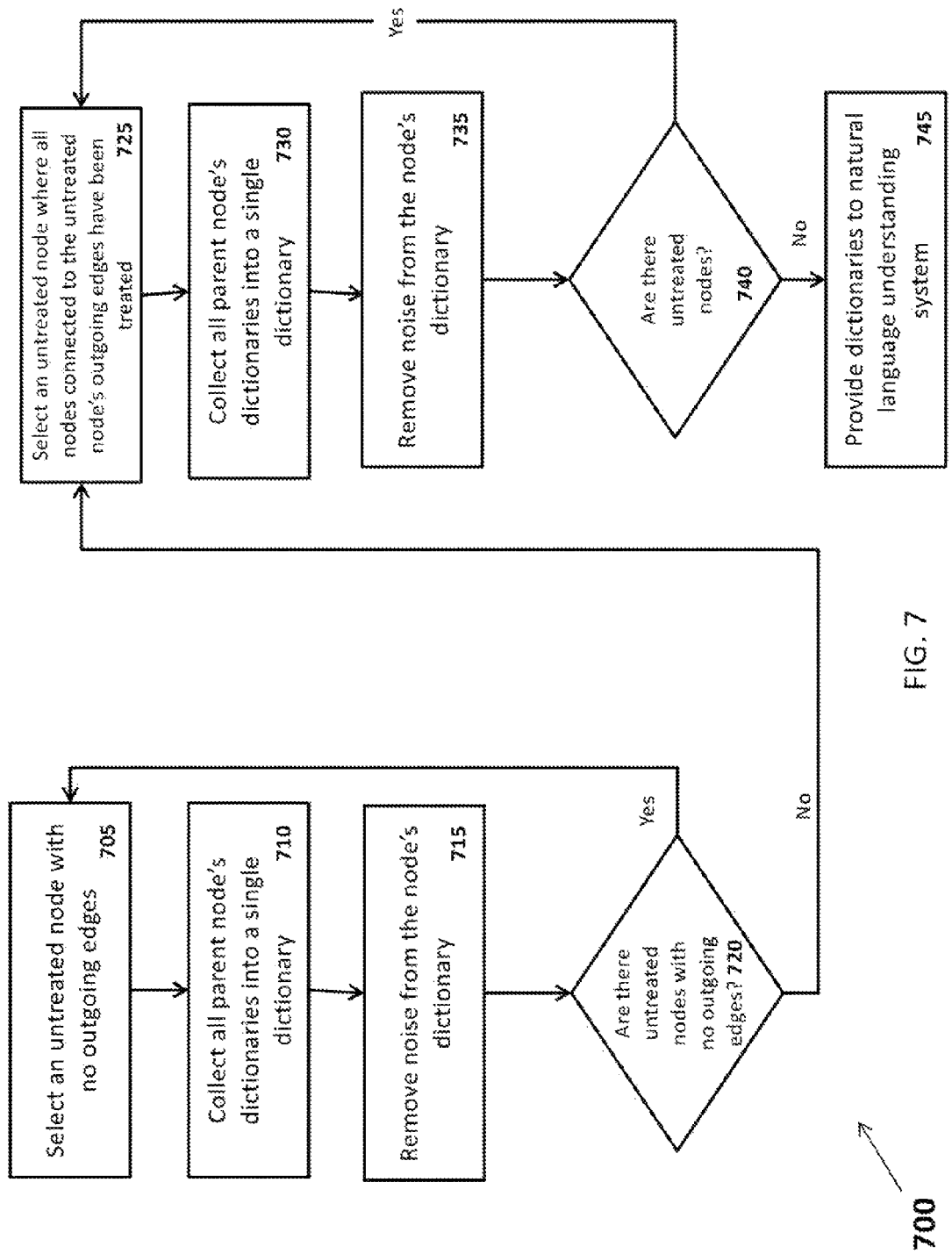

FIG. 7 illustrates a method 700 of removing noise from dictionaries by following an ordering determined from the resulting acyclic dependency graph. The method may begin with a noise reducing agent first selecting an untreated node with no outgoing edges (step 705). The noise reducing agent then collects all of a node's parent dictionaries into a single dictionary for the purposes of noise removal (step 710). The noise reducing agent then removes the collected dictionary's entries from the currently selected dictionary, thus "treating"

the dictionary and node (step 715). This portion of the method 700 may be repeated until there are no longer any untreated nodes with no outgoing edges (step 720). Once all nodes without outgoing edges have been treated, the noise reducing agent selects any node with outgoing edges, where all of the node's children have already been treated (step 725). The noise reducing agent collects all of the parent node dictionary entries into a single dictionary (step 730), which are removed from the currently selected node/dictionary (step 735). The method then continues to select untreated nodes where all nodes connected to the untreated node's outgoing edges have been treated (step 725) until all nodes have been treated (step 740). The noise reducing system may then provide the treated dictionaries to a CLU system or other destination (step 745).

For a selected node, the noise reducing agent collects all of the selected node's parent dictionaries into a single dictionary for purposes of noise removal. This allows the noise reducing agent to process all deletions in a single step, rather than in batches corresponding to individual parent nodes. In some embodiments, this step may be omitted.

As an illustration and referring to FIGS. 6B and 7, consider the removal strategy of method 700 applied to the determined ideal solution 620. In this example, the procedure for noise removal would be to first combine dictionaries "B" and "C" into a single dictionary. The entries from this combined dictionary would then be removed from dictionary "A". Next, the entries from dictionary "B" would be removed from dictionary "C." No entries from dictionary "B" would be removed. Put more simply, the ordering for noise removal would be to first remove "B" and "C" from "A", and then remove "B" from "C".

Having described an embodiment of the technique described herein in detail, various modifications and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A method of removing noise from a plurality of dictionaries using a graph having a plurality of vertices and a plurality of edges, the plurality of vertices including a first vertex and a second vertex, the plurality of edges including a first edge connecting the first vertex and the second vertex, the method comprising:
associating dictionaries in the plurality of dictionaries to respective vertices in the plurality of vertices, the associating comprising associating a first dictionary in the plurality of dictionaries to the first vertex and a second dictionary in the plurality of dictionaries to the second vertex, wherein the first dictionary includes a plurality of entries, the plurality of entries including multiple entries each of which comprises multiple words;
determining weights for the plurality edges at least in part by determining a first weight for the first edge based on a measure of noise between the first dictionary and the second dictionary;
selecting, using the determined weights, a subset of the plurality of edges forming an acyclic graphical representation;
determining an ordering based on the acyclic graphical representation; and
removing noise from the plurality of dictionaries according to the determined ordering.

2. The method of claim 1, wherein removing noise from the plurality of dictionaries comprises removing entries from at least some of the plurality of dictionaries.

3. The method of claim 1, wherein the plurality of dictionaries comprises a particular dictionary associated with a vertex in the acyclic graphical representation that has no outgoing edges, and wherein removing noise from the plurality of dictionaries comprises removing noise from the particular dictionary before removing noise from any dictionary associated with a vertex in the acyclic graphical representation that has at least one outgoing edge.

4. The method of claim 1, wherein selecting the subset of the plurality of edges comprises:
identifying a maximum acyclic subgraph of the graph or an approximation to the maximum acyclic subgraph of the graph.

5. The method of claim 1, further comprising automatically creating the plurality of dictionaries from an ontology.

6. The method of claim 1, further comprising:
providing the plurality of dictionaries to a language processing system after removing noise from the plurality of dictionaries.

7. The method of claim 1, wherein determining the first weight comprises determining how many entries in the first dictionary are also in the second dictionary.

8. The method of claim 1, further comprising automatically creating the plurality of dictionaries from a medical ontology.

9. A system for removing noise from a plurality of dictionaries using a graph having a plurality of vertices and a plurality of edges, the plurality of vertices including a first vertex and a second vertex, the plurality of edges including a first edge connecting the first vertex and the second vertex, the system comprising:
at least one processor configured to:
associate dictionaries in the plurality of dictionaries to respective vertices in the plurality of vertices, the associating comprising associating a first dictionary in the plurality of dictionaries to the first vertex and a second dictionary in the plurality of dictionaries to the second vertex, wherein the first dictionary includes a plurality of entries, the plurality of entries including multiple entries each of which comprises multiple words;
determine weights for the plurality edges at least in part by determining a first weight for the first edge based on a measure of noise between the first dictionary and the second dictionary;
select, using the determined weights, a subset of the plurality of edges
forming an acyclic graphical representation;
determine an ordering based on the acyclic graphical representation, and
remove noise from the plurality of dictionaries according to the determined ordering.

10. The system of claim 9, wherein the at least one processor is further configured to remove noise from the plurality of entries by removing entries from at least some of the plurality of dictionaries.

11. The system of claim 9, wherein the plurality of dictionaries comprises a particular dictionary associated with a vertex in the acyclic graphical representation that has no outgoing edges, and wherein removing noise from the plurality of dictionaries comprises removing noise from the first dictionary before removing noise from any dictionary associated with a vertex in the acyclic graphical representation that has at least one outgoing edge.

12. The system of claim 9, wherein the at least one processor is configured to select the subset of the plurality of edges by identifying a maximum acyclic subgraph of the graph or an approximation to the maximum acyclic subgraph of the graph.

13. The system of claim 9, wherein the at least one processor is further configured to create the plurality of dictionaries from an ontology.

14. The system of claim 9, wherein the at least one processor is further configured to provide the plurality of dictionaries to a language understanding system.

15. The system of claim 9, wherein the at least one processor is configured to determine the first weight at least in part by determining how many entries in the first dictionary are also in the second dictionary.

16. The system of claim 9, wherein the at least one processor is further configured to create the plurality of dictionaries from a medical ontology.

17. A device storing software that, when executed by a computing device, controls the computing device to perform a method of removing noise from a plurality of dictionaries using a graph having a plurality of vertices and a plurality of edges, the plurality of vertices including a first vertex and a second vertex, the plurality of edges including a first edge connecting the first vertex and the second vertex, the method comprising:

associating dictionaries in the plurality of dictionaries to respective vertices in the plurality of vertices, the associating comprising associating a first dictionary in the plurality of dictionaries to the first vertex and a second dictionary in the plurality of dictionaries to the second vertex, wherein the first dictionary includes a plurality of entries, the plurality of entries including multiple entries each of which comprises multiple words;

determining weights for the plurality edges at least in part by determining a first weight for the first edge based on a measure of noise between the first dictionary and the second dictionary;

selecting, using the determined weights, a subset of the plurality of edges forming an acyclic graphical representation;

determining an ordering based on the acyclic graphical representation; and removing noise from the plurality of dictionaries according to the determined ordering.

18. The device of claim 17, wherein selecting the subset of the plurality of edges comprises identifying a maximum acyclic subgraph of the graph or an approximation to the maximum acyclic subgraph of the graph.

19. The device of claim 17, wherein determining the first weight comprises determining how many entries in the first dictionary are also in the second dictionary.

20. The device of claim 17, wherein the method further comprises automatically creating the plurality of dictionaries from a medical ontology.

* * * * *